United States Patent [19]

Privalov et al.

[11] 4,069,225
[45] Jan. 17, 1978

[54] 3-(1-HYDROXYETHYL)IMINO-1,2,4-DITHIAZOLIDINE-5-THIONE

[76] Inventors: Vasily Efimovich Privalov, ulitsa Kostomarovskaya, 5/7, kv. 15; Evgeny Iosifovich Vail, Tobolskaya ulitsa, 52, kv. 36; Andrei Mefodievich Khanin, ulitsa Vesnina, 12, kv. 52; Evgeny Ivanovich Gromov, ulitsa Vesnina, 12, kv. 32; Viktoria Mikhailovna Petropolskaya, ulitsa 23 Avgusta, 29, kv. 45; Lidia Mikhailovna Agarkova, ulitsa Vesnina, 12, kv. 11, all of Kharkov, U.S.S.R.

[21] Appl. No.: 252,455

[22] Filed: May 11, 1972

[51] Int. Cl.$^2$ .............................. C07D 285/00
[52] U.S. Cl. ....................... 260/306.8 R; 252/150; 252/391
[58] Field of Search ........................... 260/306.8 R

[56] References Cited
U.S. PATENT DOCUMENTS 2,971,909  2/1961  Fields ........................ 260/306.8 R
3,621,030  11/1971  Seltzer ........................ 260/306.8 R Primary Examiner—R. Gallagher
Attorney, Agent, or Firm—Haseltine, Lake & Waters

[57] ABSTRACT

A new corrosion inhibitor for acid-pickled ferrous and nonferrous metals in the form of isoperthiocyanic and its α-hydroxy-substituted derivatives of the formula

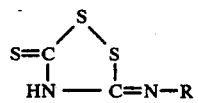

where R is

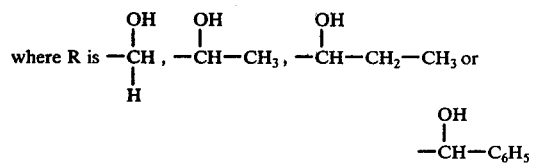

The metals are pickled in aqueous solutions of acid mixed with 0.1-1 wt.-% of said inhibitor.

1 Claim, No Drawings

3-(1-HYDROXYETHYL)IMINO-1,2,4-DITHIAZOLI-DINE-5-THIONE

The present invention relates to protection of metals against corrosion and more specifically it relates to corrosion inhibitors for acid-pickled ferrous and non-ferrous metals.

It is known that after heat treatment or prolonged contact of ferrous and non-ferrous metals with air said metals are covered with a layer of scale which has to be removed before machining.

This descaling of the metal surface is carried out, as a rule, by pickling the metal in solutions of acids, mainly sulfuric, muriatic, phosphoric, nitric, etc.

For this purpose the articles (sheets, wire, pipes, shaped articles, etc.) of ferrous or non-ferrous metals are immersed in a pickling bath which is an aqueous solution of acid or a mixture of acids with various additives and held in said solutions as long as is required for complete removal of scale.

Inasmuch as the thickness of the scale throughout the surface of an article varies, the entire surface is not descaled simultaneously. At some points of the surface the scale is removed while the other points are still covered with scale. As a result, pure metal begins to be dissolved at the descaled points. Metal may also be dissolved if the articles are held too long in the pickling bath which is inevitable in the pickling practice. Dissolution of the metal in the course of pickling is highly undesirable as it leads to excessive consumption of acid and to losses of metal.

To get rid of the unwanted processed during pickling, the pickling solutions are usually mixed with a small quantity (under 1%) of substances which retard the dissolution of metal. These substances are called corrosion inhibitors.

The corrosion inhibitors used in metal pickling practice are various organic and inorganic substances. The most effective of them are organic compounds whose functional groups include the atoms of hydrogen, sulfur, oxygen and compounds with multiple bonds.

Known in the art as a corrosion inhibitor is para-dodecylbenzylpyridine chloride (S.A. Balezin e.a. "Protection of Metals" 1, No. 3, 337, 1965) noted for high protective properties. However, the complex synthesis of this inhibitor and scarcity of the raw materials limit its wide application in pickling of metals.

Also recommended as a corrosion inhibitor for pickling ferrous metals in acids is a mixture of acetylene alcohol of the formula $RC{\equiv}CCR_2OH$ (where R — H, alkyl, phenyl or hydroxyalkyl) with pyridine derivatives (U.S. Pat. No. 3107221 Apr. 18, 1958). The disadvantages of this inhibitor include high cost, complexity of manufacture and difficult handling since its introduction into the pickling bath cells for adding surface-active agents which are resistant to acids.

An object of the present invention is to provide an inhibitor which, along with a high efficiency, would be made from readily available materials, would be cheap, free of unpleasant odors, non-toxic, would not complicate the process of pickling, would not form sludge, would be readily soluble in the pickling bath and would not deteriorate the metal after pickling.

This object is accomplished by providing corrosion inhibitors for acid-pickled ferrous and non-ferrous metals in the form of substances which, according to the invention, consist of isoperthiocyanic acid or α-hydroxylated derivatives thereof with a general formula: $HN_2C_2S_3R$

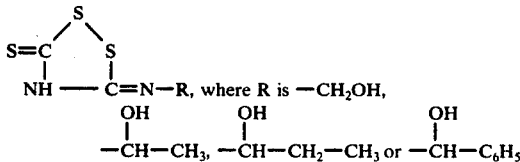

where R is $-CH_2OH$, $-CH-CH_3$ with OH, $-CH-CH_2-CH_3$ with OH or $-CH-C_6H_5$ with OH A method of protecting said metals against corrosion in the process of their pickling with acids consists, according to the invention, in that the metals are pickled with acid solutions containing 0.1–1% of the corrosion inhibitor, i.e. isoperthiocyanic acid or the above-mentioned α-hydroxylated derivatives thereof.

According to its chemical nature, isoperthiocyanic acid (3-amino-5-thiono-1, 2. 4-dithiazole) belongs to the class of thiazoline compounds. It is an odorless light-yellow crystalline powder readily soluble in solutions of acids and alkalies and in some organic solvents. It is poorly dissolved in cold water and alcohol. Solubility in water increases with heating. When melted, it decomposes. The inhibiting effect of isoperthiocyanic acid manifests itself immediately after dissolution in acids. The protection effect of this inhibitor for carbon steel at 80° C in solutions of sulfuric, phosphoric, muriatic and acetic acids reaches 97–99%.

The protective effect of isoperthiocyanic acid and its derivatives is produced because the molecules of these compounds contain amide and thione groups as well as double bonds which are conducive to the adsorption of these compounds on the active areas of the metal surface, creating a high energy barrier for the reaction of metal ionization and for the discharge of hydrogen ions.

The presence of a hydroxylated group in the α-hydroxylated derivatives of isoperthiocyanic acid increases the solubility of these compounds in water and weak acid solutions by the creation of hydrogen bonds between the hydroxyl groups and the molecules of water. This widens the range of acid concentrations within which the protective effect of these inhibitors can manifest itself.

The present invention ensures the results required in acid-pickling of metals.

The use of isoperthiocyanic acid and its α-hydroxylated derivatives slows down effectively the corrosion of the base metal, cuts down the consumption of acid because the latter is not used for dissolving the pure metal, reduces the losses of the base metal; at the same time it does not decrease the scale dissolution rate, does not produce sludge due to interaction of scale with the inhibitor, and the pickling process is not accompanied by the liberation of toxic substances harmful to life.

The surface of metal after pickling in presence of the inhibitor is smooth, bright and free of pitting. The physical state of the inhibitors makes them suitable for transportation and metering.

The inhibitors are readily available and cheap materials, easily produced from the by-products of coke industry and the industry of organic synthesis.

For example, isoperthiocyanic acid can be obtained by the interaction of the salts of thiocyanic acid ($NH_4CNS$, $NaCNS$, etc.) with sulfuric acid according to the following reaction:

$$2NH_4CNS + H_2SO_4 \rightarrow 2HCNS + (NH_4)_2SO_4$$

3HCNS → H₂C₂N₂S₃ + HCN
isoperthiocyanic acid

The thiocyanates, in turn, are obtained as by-products in cleaning the coke gas of hydrogen cyanide.

The α-hydroxylated derivatives of isoperthiocyanic acid can be produced by condensing the latter with aliphatic or aromatic aldehydes.

To make the present invention more apparent to those skilled in the art we hereby submit the actual examples of using said compounds in the capacity of inhibitors.

EXAMPLE 1

Carbon steel specimens in the form of plates 100×100×5 mm covered with scale were pickled in solutions of sulfuric, muriatic, acetic and orthophosphoric acids with 0.1 wt.-% of isoperthiocyanic acid (with respect to the weight of the pickling acid). For better demonstration of the inhibiting effect, the pickling time (4 hours) was much longer than necessary for the complete removal of scale. An objective estimate of the inhibiting effect was determined by the coefficient of protective effect calculated by the formula:

$$Z\% = \frac{K_o - K_1}{K_o} \cdot 100$$

and the coefficient of inhibition calculated by the formula:

$$\gamma = K_1/K_o$$

where
$K_1$ = corrosion rate of metal in presence of inhibitor, g/m²-hr
$K_o$ = corrosion rate of metal without inhibitor, g/m²-hr The results of tests are summarized in Table 1.

Table 1

| Acid | Acid concentration, % | Temperature, °C | Corrosion rate W/o inhibitor, g/m²-hr | Corrosion rate with inhibitor g/m²-hr+ | Coefficient of protective effect % | Coefficient of inhibition γ |
|---|---|---|---|---|---|---|
| 1. Sulfuric | 50 | 25 | 110 | 0.6 | 99.2 | 184 |
| 2. Sulfuric | 60 | 60 | 704 | 2.4 | 99.7 | 293 |
| 3. Ortho-phosphoric | 50 | 60 | 1041 | 9.9 | 99.4 | 105 |
| 4. Acetic | 50 | 60 | 109 | 3.8 | 96.7 | 29 |
| 5. Muriatic | 27 | 25 | 210 | 2.9 | 98.5 | 10 |

The pickling time was considerably longer than required for the removal of scale and still the protective effect of the inhibitor was sufficiently high for protecting the metal against dissolution both at low and high temperatures.

It must be noted that the protective effect was observed both in mineral and organic acids.

EXAMPLE 2

Carbon steel specimens in the form of plates 100×100×5 mm covered with scale were pickled in acid solutions with 0.1 wt.-% of inhibitor, i.e. 3-hydroxymethylisoperthiocyanate
(with respect to the weight of the pickling acid).

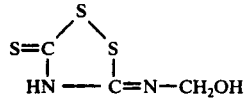

The effect of inhibitors was estimated as in Example 1 by coefficients Z and γ. Pickling time 1 hour, temperature 80° C. The results of tests are summarized in Table 2.

Table 2

| Acid | Acid concentration, % | Corrosion rate w/o inhibitor, g/m²-hr | Corrosion rate with inhibitor, g/m²-hr | Coefficient of protective % effect, | Coefficient of inhibition γ |
|---|---|---|---|---|---|
| 1. Sulfuric | 50 | 980 | 3.9 | 99.7 | 251 |
| 2. Ortho-phosphoric | 50 | 1200 | 9.7 | 99.4 | 1240 |
| 3. Acetic | 50 | 130 | 2.5 | 98.1 | 52 |
| 4. Muriatic | 27 | 850 | 9.4 | 98.9 | 197 |

The data of the table prove that 3-formylisoperthiocyanate produces a high protective effect at 80° C which testifies to a high resistance of the inhibitor in hot acid.

EXAMPLE 3

Carbon steel specimens in the form of pipes of 33 mm diameter, 500 mm long, covered with scale have been pickled in acid solutions with 0.1 wt.-% of inhibitor, i.e. 3-α-hydroxy-ethylisoperthiocyanate

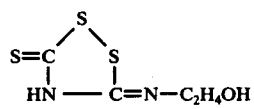

(with respect to the weight of the pickling acid). Pickling time 1 hour. Solution temperature 80° C. The results of tests are given in Table 3.

Table 3

| Acid | Acid concentration, % | Corrosion rate w/o inhibitor, g/m²-hr | Corrosion rate with inhibitor, g/m²-hr | Coefficient of protective effect, % | Coefficient of inhibition γ |
|---|---|---|---|---|---|
| Sulfuric | 50 | 980 | 3.8 | 99.8 | 252 |
| Phosphoric | 50 | 1200 | 9.8 | 99.2 | 1225 |
| Acetic | 50 | 130 | 2.4 | 98.2 | 54 |
| Muriatic | 27 | 850 | 4.5 | 99.6 | 189 |

A comparative analysis of the data given in Tables 3 and 2 proves that the protective effect of the methylol and ethylol derivatives of isoperthiocyanic acid is approximately the same.

EXAMPLE 4

Specimens of stainless steel 18XH4BA in the form of cylinders of 100 mm diameter, 150 mm long, were pickled in 20% sulfuric acid at 60° C with 0.1 wt.-% isoperthiocyanic acid. After 3 hours of pickling the coefficient of protective effect Z was 99% and the coefficient of inhibition $\gamma = 106$.

The surface of the cylinders was bright, smooth, without pitting corrosion.

This example proves that the inhibitor is effective in the case of stainless steels too.

EXAMPLE 5

Coils of rolled wire of 10 mm diameter weighing 30 tons were pickled in sulfuric acid (23 wt.-%) with 1.5 kg/m³ 3-hydroxymethylisoperthiocyanate at 74° C. In the course of pickling, measurements were made of the amount of solution in the pickling bath, concentration of acid and iron sulfate. The results of measurements are given in Table 4.

Table 4

| Weight of pickled metal,t | Bath capacity,m³ | | Concentration of FeSO₄ | | Weight of produced FeSO₄, kg | Weight of spent sulfuric acid,kg | Sulfuric acid consumption, kg/t |
|---|---|---|---|---|---|---|---|
| | Before pickling | After pickling | Before, pickling, g/l | After pickling, g/l | | | |
| 30 | 6.8 | 6.7 | 10 | 167 | 1052 | 677.5 | 22.6 |

It can be seen from this table that the consumption of sulphuric acid per ton of pickled metal is a mere 22.6 kg.

EXAMPLE 6

A copper tube of 12/10 mm diameter has been immersed into 20% boiling sulphuric acid with 0.05% of isoperthiocyanic acid. After 2 hours of boiling there were no losses in the weight of the specimens. On immersing a copper tube of 10/12 mm diameter into 20% boiling sulfuric acid without the inhibitor, the corrosion rate reached 8 g/m²-hr This proves that introduction of the inhibitor into sulfuric acid ensures full protection of copper against dissolution.

EXAMPLE 7

Carbon steel specimens of a special shape 10×10×50 mm in size were pickled in 20% sulfuric acid at 50° C with isoperthiocyanic acid added. Pickling time 1 hour. After pickling, the specimens were tested for impact strength on a pendulum impact-testing machine. The results of the tests are given in Table 5.

Table 5

| Composition of pickling solution | Pickling time, min | Temp., ° C | Impact strength, kgm/cm² | Remarks |
|---|---|---|---|---|
| 20% sulfuric acid | 30 | 70 | 8.86 | Column 5 gives arithmetical mean of 5 measurements |
| 20% sulfuric acid with inhibitor | 30 | 70 | 10.6 | An impact strength of 10.6 kgm/cm² refers to reference specimens |

The data of this table make it possible to conclude that pickling with an inhibitor does not cause absorption of hydrogen by metal and is not accompanied by hydrogen enbrittlement.

What is claimed is:
1. A compound of the formula

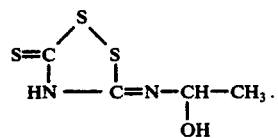

* * * * *